United States Patent [19]

Cabasso et al.

[11] Patent Number: 5,449,736

[45] Date of Patent: Sep. 12, 1995

[54] WATER SOLUBLE PHOSPHORYLATED POLYSILOXANES

[75] Inventors: Israel Cabasso; Shi Lin, both of Syracuse, N.Y.

[73] Assignee: Research Foundation Of The State of New York, Albany, N.Y.

[21] Appl. No.: 93,185

[22] Filed: Jul. 16, 1993

[51] Int. Cl.$^6$ .............. C07D 319/06; C07F 7/18; C07F 9/40; C08G 77/395
[52] U.S. Cl. ...................... 528/25; 528/27; 549/214; 556/405
[58] Field of Search .............. 528/25, 27; 549/214; 556/405

[56] References Cited

U.S. PATENT DOCUMENTS

| | | |
|---|---|---|
| 2,843,615 | 7/1958 | Linville . |
| 4,093,641 | 6/1978 | Plueddemann ............ 556/405 |
| 4,514,342 | 4/1985 | Billington et al. . |
| 4,629,602 | 12/1986 | Gousetis et al. . |
| 4,781,733 | 11/1988 | Babcock et al. . |
| 4,784,918 | 11/1988 | Klett et al. . |

FOREIGN PATENT DOCUMENTS

925722  5/1963  United Kingdom ............ 556/405

OTHER PUBLICATIONS

Cabasso, I., et al. "Synthesis and Characterization of Monomers and Polymers of Acryalted Phosphonate Esters Derived from Glycerol, D-Mannitol, D-Sorbitol, Pentaerythritol and Dipentaerythritol" Journal of Polymer Science, vol. 26, pp. 2997–3014 (1988).

Fish, D., et al. "Conductivity of solid complexes of lithium perchlorate with poly {[w-methoxyhexa (oxyethylene) ethoxyl methylsiloxane}" Makromol. Chem., Rapid Commun., vol. 7, pp. 115–120 (1986).

Bannister, D. J., et al. "A Water–Soluble Siloxane: Poly(ethylene glycol) comb Polymer." Journal of Polymer Schience, vol. 26, pp. 465–467 (1985).

Karayannis, N. M., et al. "Neutral Organophosphorous Chalcogenide–metal Salt Interactions: Addition and Decomposition Products" Inorganica Chimica Acta Reviews, pp. 69–105 (1971).

Juengst, C. D., et al. "Preparation and Properties of Dimethyl Phosphonomethyl Methylsiloxane Dimethylsiloxane Copolymers" Journal of Polymer Science, vol. 25, 1967–1978 (1987).

Kohama, S., et al. "Alcoholysis of Poly(methylhydrogensiloxane)" Journal of Applied Polymer Science, vol. 21, pp. 863–867 (1977).

*Primary Examiner*—John C. Bleutge
*Assistant Examiner*—D. R. Wilson
*Attorney, Agent, or Firm*—Morgan & Finnegan

[57] ABSTRACT

This invention relates to a novel family of phosphorylated polysiloxanes which are non-ionic and water soluble. When these polysiloxanes are dissolved in water, the resulting solutions exhibit low surface tensions. The invention also relates to phosphorylated polysiloxanes which are gels or hydrogels. The invention further contemplates methods of synthesizing the phosphorylated polysiloxanes.

2 Claims, No Drawings

WATER SOLUBLE PHOSPHORYLATED POLYSILOXANES

BACKGROUND OF THE INVENTION

Polysiloxane fluids and elastomers are well known and are generally composed of linear polyorganosiloxanes of the following formula:

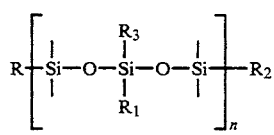

Polysiloxane fluids are known for their thermal stability and hydrophobicity. They can be synthesized so that they will have different viscosities which make them very useful as lubricants at very high temperatures. When crosslinked the polysiloxane fluids become elastomeric in nature. These elastomers have found widespread use due to their special properties. These unique properties include good dielectric properties and resistance to deformation at both high and low temperatures. For example, these compounds have been found to be useful as electrical insulators. Additionally, silicone elastomers have a high gas permeability, leading to their extensive use as membranes for gas separation and purification.

A large number of methods are available for the production of polyorganosiloxanes from monomeric organosiloxanes. The process most frequently used is the hydrolysis of the functional groups attached to the silicon atom, for example, hydrolysis of various silanes to form silanols, which condense spontaneously to form siloxanes.

The synthesis of poly(methylhydrogensiloxane) ("PMHS") has been achieved by the hydrolysis of methylhydrogen-dichlorosilane followed by a silanol condensation reaction. Derivatives of PMHS have also been synthesized. For example, poly(methylalkoxysiloxane) has been prepared by reacting PMHS with various low molecular weight alcohols in the presence of various basic catalysts (See S. Kohama and Y. Umeki, *J. Appl. Polym. Sci.*, 21, 863 (1977)). Additionally, a novel polysiloxane having poly(ethylene glycol) side groups has been prepared by reacting methoxy poly(ethylene glycol) with PMHS employing triethylamine as a catalyst (See D. J. Bannister, M. Doyle and D. R. Macfarlane, *J. Polym. Sci.: Polym. Let. Ed.*, 23, 465 (1985)). Recently, poly{[ω-methoxyhexa(oxyethylene)ethoxy]-methylsiloxane} was prepared by reacting PMHS with methoxypoly(ethylene glycol) at 60° C. using zinc octanoate as the catalyst and tetrahydrofuran as the solvent (See D. Fish, I. M. Khan and J. Smid, *Makromol. Chem., Rapid Comm.*, 7, 115 (1986)).

Organo phosphates, phosphonates and other compounds containing phosphoryl moieties are known to be strong electrondonating groups, and therefore are know for their: chelating and adhesive properties, electrochemical passivation and corrosion inhibition.

It would be of interest to synthesize phosphorylated derivatives of polysiloxanes. In this specification, we describe the synthesis of such compounds which were found to be hydrophilic. The hydrophilic nature of such derivatives does not result from hydroxyls or ionic moieties, but results from the presence of the non-ionic, hydrogen accepting phosphoryl groups. Information regarding the synthesis of organophosphorus polysiloxanes is limited. The synthesis of dimethyl phosphonomethyl methylsiloxane dimethylsiloxane copolymers from the siloxane monomer was only recently disclosed (C. P. Juengst and W. Weber, (*J. Polym. Sci.: Polym. Chem., Ed.* 25, 1967 (1987)), however, very low yields were obtained.

SUMMARY OF THE INVENTION

It has been discovered that various water soluble phosphorylated polysiloxane derivatives can be synthesized. Accordingly, it is an object of this invention to provide novel phosphorylated polysiloxane derivatives which are soluble in water. Another object of this invention is provide phosphorylated polysiloxane derivatives which when dissolved in water form solutions which exhibit low surface tension. It is a further object of this invention to provide phosphorylated polysiloxane derivatives which can be formed into gels or hydrogels.

Another object of this invention is to provide phosphorylated polysiloxane derivatives which can be used to form complexes with uranium salts, as well as salts of metals from the actinide and lanthinide series.

A further object of this invention is to provide a method of synthesizing the phosphorylated polysiloxane derivatives contemplated by this invention.

These objects, as well as others, which will become apparent from the description which follows, are achieved by phosphorylated polysiloxane derivatives represented by the following formulas:

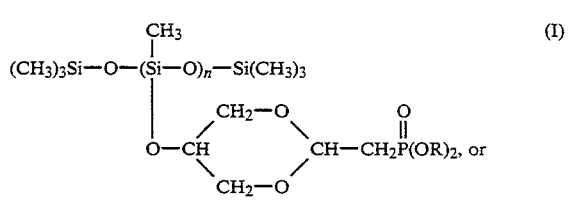

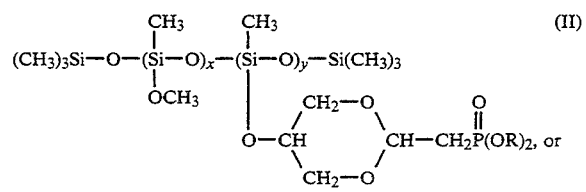

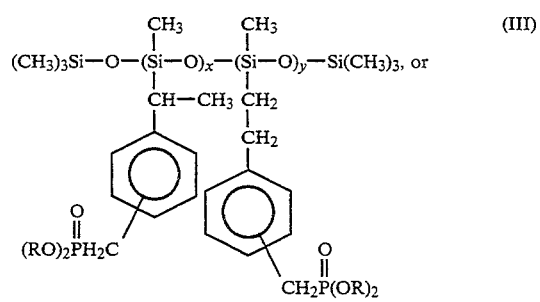

-continued

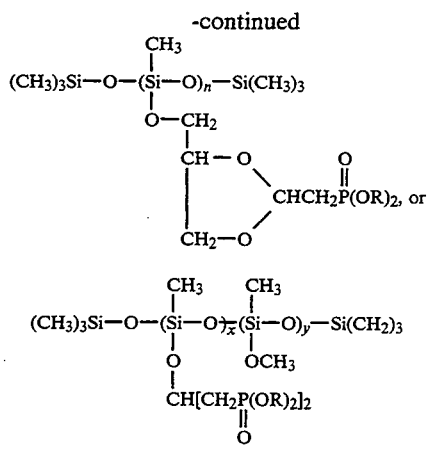

(IV)

(V)

where R is a straight-chain or branched alkyl radical having up to eight carbon atoms and n, x and y are each independently integers between 1 and 10,000. The polymers represented by Formulas I through V are not crosslinked when prepared as described hereafter. However, the polymers represented by Formulas I through V may be crosslinked to form gels or hydrogels when desired.

This invention also contemplates phosphorylated polysiloxane derivatives synthesized by the condensation reaction of poly(methylhydrogensiloxane) ("PMHS") with phosphonates derived from D-mannitol (Formulas VI and VII), D-sorbitol (Formula VIII), dipentaerythritol (Formula IX), and pentaerythritol (Formula X).

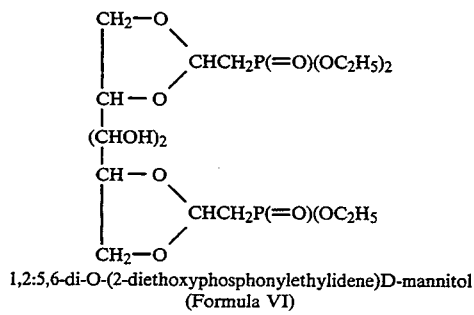

1,2:5,6-di-O-(2-diethoxyphosphonylethylidene)D-mannitol
(Formula VI)

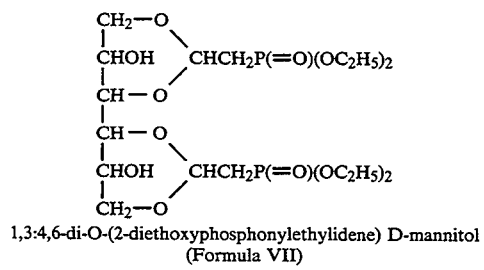

1,3:4,6-di-O-(2-diethoxyphosphonylethylidene) D-mannitol
(Formula VII)

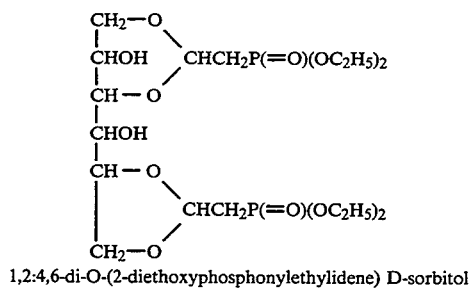

1,2:4,6-di-O-(2-diethoxyphosphonylethylidene) D-sorbitol

-continued
(Formula VIII)

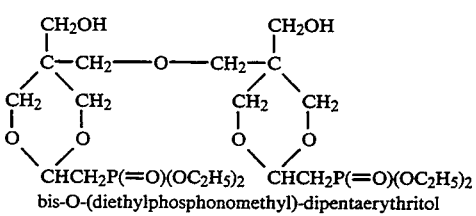

bis-O-(diethylphosphonomethyl)-dipentaerythritol
(Formula IX)

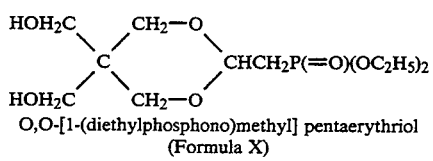

O,O-[1-(diethylphosphono)methyl] pentaerythriol
(Formula X)

DETAILED DESCRIPTION OF THE INVENTION

This invention relates to novel phosphorylated polysiloxanes and methods of synthesizing these polymers. The phosphorylated polysiloxanes contemplated by this invention are unique in that they are non-ionic and water soluble. Additionally, the phosphorylated polysiloxanes of this invention can be used to form aqueous solutions which exhibit low surface tension.

The phosphorylated polysiloxanes contemplated by this invention are viscous liquids which can be handled easily and conveniently. Furthermore, the phosphorylated polysiloxanes disclosed by this invention exhibit low critical solution temperatures ("LCST"), which makes them progressively more soluble in cold water but allows them to separate into separate and distinguishable phases at elevated temperatures. For example, poly {5-oxy [2', 2'-diethoxphosphonomethyl)-1, 3-dioxane]methysiloxane} ("POMS") is partially miscible in water at ambient temperature. However, the solubility of POMS in water increases as the temperature decreases. Below a certain critical temperature, POMS and water are completedly miscible. This unique property is reversible. As the temperature of the solution increases, the solubility of POMS in water decreases. This unpredictable and rare property can be found in only a few polymers such as some derivatives of poly(ethylene oxide), and if at all, with other polymers that are inherently liquids above 1,000 daltons.

The phosphorylated polysiloxanes contemplated by this invention have numerous applications. For example, when aqueous solutions of the polysiloxanes of this invention are formed, the resulting solutions exhibit low surface tension. For example, aqueous solutions containing about 0.1 to about 0,001% phosphorylated polysiloxanes contemplated by this invention exhibit surface tensions less than about 40 dynes/cm. Therefore, aqueous solutions with low concentrations of the phosphorylated polysiloxanes of this invention can wet surfaces which under normal conditions either can not easily wet or repels water.

The LCST behavior of the phosphorylated polysiloxanes of this invention also make them extremely useful in optical and electrical switches, as well as numerous other temperature controlled applications. For example, these polymers can be used as temperature detectors or thermosensors. In one particular application, they can be used as a fever indicator. The cloud point of 60% POMS and water is about 37° C. If the temperature of the human body is normal, the solution will remain clear if touched. If the body temperature is above normal, the solution will become cloudy when touched.

These polysiloxanes can also be used to chelate transition metal salts and can form stable complexes with uranium salts. The chelated metal salts and complexes are useful in the plating industry and in nuclear fuel processing. The polymers contemplated by this invention may also be used in the formation of complexes with salts of the metals of the transition, actinide and lanthanide series. This property is particularly useful when these compounds are used as corrosion inhibitors in paints. Moreover, the phosphorylated polysiloxanes may be useful as medical implants where radiopacity of the implant material due to the presence of a heavy metal salt is required.

Additionally, the polymers contemplated by this invention may be used as textile treatments, photolithography, adhesives and for the prevention of dental caries. Furthermore, these materials can be crosslinked to form gels or hydrogels for bio-applications.

The phosphorylated polysiloxanes represented by Formula I may be synthesized by the following process:
a) reacting bromoacetaldehyde diethyl acetal and a phosphorous ester having the Formula A

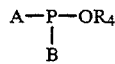

wherein A and B may be independently a primary alkoxy, secondary alkoxy, alkyl or aryloxy group with up to four carbons and $R_4$ is a lower alkyl group, typically a $C_1$–$C_3$ alkyl, to form compound 1,

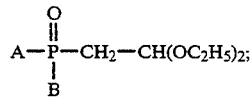

b) reacting compound 1 with glycerol at a temperature of about 25° C. to about 100° C. in the presence of a mineral acid catalyst such as hydrochloric or sulfuric acid to form compound 2,

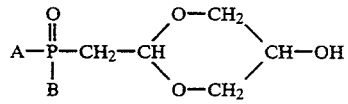

c) reacting compound 2 and poly (methylhydrogensiloxane) ("PMHS") at a temperature of about 25° C. to about 100° C. in the presence of a condensation catalyst to form a phosphorylated polysiloxane represented by Formula I.

The phosphorylated polysiloxanes represented by Formula II may be synthesized by the following process:
d) synthesizing compound 2 which was prepared as described previously; and
e) reacting compound 2 and poly (methylhydrogensiloxane) ("PMHS") at a temperature of about 25° C. to about 100° C. in the presence of a condensation catalyst and then reacting methanol with the remaining unreacted copolymer Si-H groups at a temperature of about 25° C. to about 60° C. to form a phosphorylated polysiloxane represented by Formula II.

The catalysts which may be used in the reactions described in step (c) between compound 2 and PMHS, and in step (e) between methanol and PMHS include metal salt catalysts such as zinc octanoate or tin octanoate; inorganic catalysts such as sodium carbonate, potassium carbonate, sodium silicate, sodium hydrogen carbonate, barium carbonate, magnesium carbonate, magnesium chloride, cadmium chloride or nickel chloride; and amine catalysts such as triethylamine.

The reaction time for the reactions previously described in steps (c) and (e) may range from approximately 0.1 hours to up to one month. The length of reaction determines the degree of substitution of Si-H by the phosphorylated derivative.

Typical phosphorylated polysiloxanes represented by Formula I include: poly {5-oxy[2-(2',2'-dimethoxyphosphonomethyl)-1,3-dioxane]methylsiloxane}; poly {5-oxy[2-(2', 2',-diethyoxyphosphonomethyl)1-,3-dioxane]methylsiloxane}; and poly {5-oxy [2-(2',2'dipropoxy-phosphonomethyl)-1,3-dioxane]methylsiloxane}.

Typical phosphorylated polysiloxanes represented by Formula II include: copolymers of methoxy methyl siloxane with the phosphorylated siloxanes represented by Formula I.

The phosphorylated polysiloxanes represented by Formula III may be synthesized by the following process:
a) reacting vinylbenzylchloride ("VBC") and PMHS in the presence of a hydrosilyation catalyst at a temperature of about 65° C. to about 120° C. in a solvent media or in bulk to form compound 3, a poly [(chlorobenzyl) α,β-ethyl methylsiloxane]; and
b) reacting compound 3 with a phosphorous ester of the type represented by formula A and described earlier, at temperature of about 100° C. to about 200° C. for about 2 to about 10 hours to yield a phosphorylated polysiloxane represented by Formula III.

The phosphorylated polysiloxanes of Formula III may also be synthesized by:
a) reacting "VBC" and methylhydrocyclosiloxane ("MHCS") in the presence of a hydrosilyation catalyst at a temperature of about 30° C. to about 120° C. in a solvent media or in bulk to form methyl (chlorobenzyl) α,β-ethyl cyclosiloxanes ("MCECS");
b) reacting MCECS with a phosphorous ester of the type represented by formula A and described earlier to yield a phosphorylated cyclosiloxane; and
c) polymerizing the phosphorylated cyclosiloxane to form a phosphorylated polysiloxane represented by Formula III.

The hydrosilation catalysts which may be used in the earlier described steps (a) of the synthesis used to form the phosphorylated polysiloxanes represented by Formula III include: platinum-divinyltetramethyldisiloxane complex; platinum on carbon; chloroplatinic acid; a solution of platinic acid in alcohol; a solution of chloroplatinic acid in ether; complexes of platinum derivatives with various unsaturated compounds such as ethylene; platinum complexes on inorganic and organic polymeric carriers such as polymeric platinum chelates with di-(8-hydroxy-5-quinolinyl) methane; palladium complexes such as (Ph3P)4Pd; rhodium complexes such as [RhCl(CO2)]2; nickel complexes such as (Ph3P)2NiCl2; and peroxides such as dicyclohexyl peroxycarbonate. Solvents which can be used in the earlier described steps (a) include aromatic hydrocarbons such as toluene, xylene and benzene, and chlorinated hydrocarbons such as 1, 2-dichloroethane and ethers such as tetrahydrofuran and p-dioxane.

The hydrosilation reaction of the earlier described steps (a) of the synthesis of the polysiloxanes of Formula III can be conducted by a known process (E. Lukevics, et al., Organometallic Chem. Rev., J. of Organometallic Chem. Library, 51 Ed. D. Seyferth, A. G. Davies, E. O. Fisher, J. F. Normant and O. A. Revtov, 1977 pp. 1–179). The most preferred catalyst for this reaction is chloroplatinic acid and its complexes with unsaturated compounds.

It has been found that the hydrosilation reaction of the earlier described steps (a) between vinylbenzyl diethylphosphonate ester and PMHS, can yield a cross-linked product. This is caused by the reaction of the catalyst with PMHS. Present studies demonstrate that the temperature of reaction is the key to avoiding cross-linking. For example, at 56° C. the hydrosilation reaction of VBC using platinum-divinyltetramethyldisiloxane complex as the catalyst results in a cross-linked product. However, at about 72°–77° C. the reaction is found to be complete without any crosslinking after about 48 hours. This was confirmed by IR analysis of PMHS with the disappearance of the typical Si-H absorption band at 2160 cm$^{-1}$.

Typical phosphorylated polysiloxanes which can be prepared by the above process and which are contemplated by Formula III include: poly {[(dimethylphosphonobenzyl)$\alpha,\beta$-ethyl]methyl-siloxane}; poly {[(diethylphosphonobenzyl)$\alpha,\beta$-ethyl]methyl-siloxane}; poly {[(dipropylphosphonobenzyl)$\alpha,\beta$-ethyl]methyl-siloxane}, and the like.

The phosphorylated polysiloxanes of this invention which are represented by Formula IV may be synthesized by the following process:

a) reacting bromoacetaldehyde diethyl acetal and glycerol in the presence of a mineral acid catalyst such as 5-sulfosalicylic acid dihydrate to form 2-(1'-bromomethyl)4-hydroxymethyl-1,3-dioxolane, b) reacting 2-(1'-bromomethyl)4-hydroxymethyl-1,3-dioxolane) and a phosphorous ester of the type represented by Formula A and described earlier to form compound 4,

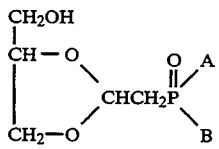

c) reacting compound 4 and PMHS at a temperature of about 25° C. to about 100° C. in the presence of a condensation catalyst as described earlier to form a phosphorylated polysiloxane represented by Formula IV.

Typical phosphorylated polysiloxanes which can be prepared by the above described process and which are represented by Formula IV include: poly{4-methoxyl[(2-dimethoxyphosphonomethyl)-1,3-dioxolane]-methyl siloxane}; poly{4-(2-diethoxyphosphonomethyl)-1,3-dioxolane]methyl siloxane}; and poly{4-methoxy[(2-dipropoxyphosphonomethyl) 1,3-dioxolane]methyl siloxane}.

The phosphorylated polysiloxanes represented by Formula V may be synthesized by the following process:

a) reacting 1,3-dibromo-2-propanol and a phosphorous ester, having the Formula A as described earlier, to form Compound 5,

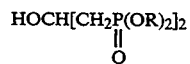

reacting Compound 5 and PMHS at a temperature of about 25° C. to about 100° C. in the presence of a condensation catalyst and then reacting methanol with the remaining unreacted copolymer Si-H groups at a temperature of approximately 25° C. to approximately 60° C. to form a phosphorylated polysiloxane represented by Formula V.

Typical phosphorylated polysiloxanes, which can be prepared by the above process and which are represented by Formula V, include: 2-propoxy-[1,3-bis(dimethoxyphosphonate)]methyl methoxymethyl siloxane copolymer; 2-propoxy-[1,3-bis(diethoxyphosphonate)]-methyl methoxy methyl siloxane copolymer; and 2-propoxy-[1,3-bis(dipropoxyphosphonate)]methyl methoxymethyl siloxane copolymer.

The synthesis of phosphorylated polysiloxanes from compounds represented by Formulas VI through X vary from the synthesis of phosphorylated polysiloxanes represented by Formulas I through V because the compounds represented by Formulas VI through X contain more than one hydroxyl group. The molecular ratio of the compounds of Formula VI through X to PMHS may be greater than one. Moreover, the reactions between PMHS and compounds of Formulas VI through X can be conducted in a more dilute solution. After about 24–48 hours, methanol can be added to react with the unreacted Si-H. Depending upon the length of reaction, the resulting products may contain about 20–80% soluble parts and 80–20% gel. Additionally, because the compounds of Formulas VI through IX have two phosphonyl groups, they may enhance the solubility of phosphorylated polysiloxanes in water.

The polymers and methods of synthesizing the polymer of this inventor are described below without, however, being limited thereto.

EXAMPLE 1

The synthesis of poly{5-oxy[2-(2',2'-diethoxy-phosphonomethyl)-1,3-dioxane]methylsiloxane}("POMS") was achieved in three steps.

Diethyl 2,2-diethoxyethyl phosphonate (compound 1) was synthesized employing the Arbuzov reaction between freshly distilled bromoacetaldehyde diethyl acetal and triethyl phosphite, as reported by Nagata et al. (See W. Nagata, T. Wakabayashi and Y. Hayase, Organic Synthesis, 53, 44 (1975)). For example, 153 grams of bromoacetaldehyde diethyl acetal was placed in a three-neck flask equipped with a magnetic stirrer. A gentle stream of nitrogen purged the system. To the stirred solution, 22.1 grams of triethylphosphite was added drop-wise over a period of approximately 25 minutes. During this time, the temperature of the solution rose from approximately 110° C. to approximately 120° C. After the addition of the triethylphosphite was complete, the mixture was stirred for about 4 hours at the temperature of about 160° C. The ethyl bromide which evolved during the reaction was recovered through a condenser. The low boiling point fractions were removed with a water pump while the residual oil was fractionated under reduced pressure at temperature of approximately 72°–79° C. The percent yield of compound 1 was about 67%.

A transacetalation reaction was then conducted between compound 1 and glycerol at about 55° C. for 24 hours in the presence of a hydrochloric acid catalyst to form 2-(2′,2′-diethoxyphosphonomethyl)-5-hydroxy-1,3-dioxane (compound 2). About 51.97 grams of compound 1 which was prepared previously in the first step was then reacted with 18.82 grams of glycerol at a temperature of about 55° C. for about 24 hours. Approximately 20 ml of hydrochloric acid was used as a catalyst. A solution of aqueous sodium hydroxide was then added to the resulting solution until a pH of 7 was reached. Compound 2 was extracted with chloroform and was dried overnight over anhydrous magnesium sulfate. Chloroform was removed by rotovapor and the viscous oil was fractionated at about 145°–147° C. and a pressure of about 0.01 mm Hg. The NMR analysis showed that Compound 2 contained about 10–25% of dioxolane derivatives (Compound 4). These derivatives can be further separated by chromatography columns. The percent yield was about 56%.

POMS was then synthesized via a condensation reaction between compound 2 and PMHS polymers having molecular weights of 2126 and 6446. The average molecular weight of PMHS used in each run was determined by 100 MHz $^1$H NMR by comparing the trimethylsiloxy end groups with the internal methyl groups to be 2126 and 6446 ($PMHS_1$ and $PMHS_2$). The synthesis for both versions of PMHS was conducted in about 30% tetrahydrofuran solution using zinc octanoate as a catalyst.

The condensation reaction is shown below:

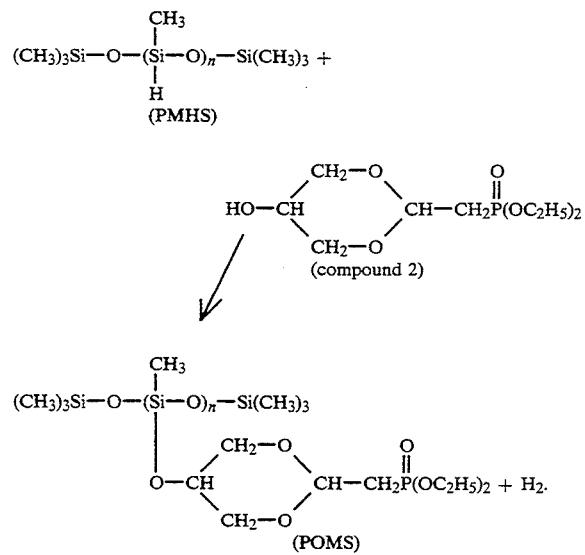

A summary of the reaction conditions and results is set forth in Table I.

TABLE I

REACTION CONDITIONS AND SUBSTITUTION PERCENT FOR CONDENSATION OF PMHS WITH COMPOUND 2

| Precursor | $M_n$ | Reaction time (hrs) | Reaction temp. (°C.) | Substitution (%) | Product |
|---|---|---|---|---|---|
| $PMHS_1$ | 2126 | 48 | 60 | >99 | $POMS_1$ |
| $PMHS_2$ | 6446 | 72 | 66 | 41 | $POMS_2$ |

Both products were analyzed by proton nuclear magnetic resonance spectroscopy ($^1$H NMR) on Varian A-60 and Varian XL-100 spectrometers using $CDCl_3$ as the solvent. The spectrum for PMHS showed a peak at 4.63 ppm, indicating the presence of the Si-H bond. However, the spectrum for $POMS_1$ showed no such peak, indicating that the condensation reaction was complete. The spectrum for $POMS_2$ showed such a peak for the Si-H bond, indicating that the condensation reaction was incomplete. The percent completion was calculated by comparing the peak observed at 4.63 ppm with the peak observed at 0.2 ppm, which represented the Si-$CH_3$ protons. Using these measurements, it was determined that the second run was only 41% complete.

The products were also analyzed by Infrared (IR) spectroscopy in the region of 4000–600 cm$^{-1}$ using a Perkin Elmer 1820 spectrometer and NaCl pellets. The extremely sensitive Si-H absorption band which appears at 2160 cm$^{-1}$ for PMHS was absent for $POMS_1$, indicating that the condensation was complete. However, a small band at 2160 cm$^{-1}$ was clearly visible for $POMS_2$, indicating that the condensation was incomplete. The reason that the second reaction did not go to completion during the same time frame as the first was most likely due to the steric factor and cyclization of the higher molecular weight of $PMHS_2$.

Assignments of the important bands of Compound 2 and POMS are shown in Table II. The slight appearance of the —OH band at 3500 cm$^{-1}$ for POMS was probably attributable to moisture absorbed by this hydrophilic polymer derivative.

TABLE 2

INFRARED ABSORPTIONS OF COMPOUND II AND POMS

| Absorption (cm$^{-1}$) | | Assignment |
|---|---|---|
| Compound II | POMS | |
| 3380 (s) | 3500* | $\nu$ O—H |
| 2976 (a) | 2976 (s) | $\nu_{as}$ $CH_3$ |
| 2920 (m) | 2926 (m) | $\nu_{as}$ $CH_2$ |
| 2898 (w) | 2898 (w) | $\nu_s$ $CH_3$ |
| 2860 (m) | 2860 (m) | $\nu_s$ $CH_2$ |
| 1470 (w) | 1475 (w) | $\delta_s$ $CH_2$ |
| 1440 (m) | 1440 (m) | $\delta_{as}$ $CH_3$ |
| 1405 (m) | 1405 (m) | $\nu$ O—C—O |
| | 1405 (w) | Asym. $CH_3$—(Si) def. |
| 1365 (w) | 1360 (w) | $\delta_s$ $CH_3$ |
| 1230 (s) | 1265 (s) | $\nu$ P=O |
| | 1240 (s) | Sym. $CH_3$—(Si) def. |
| 1145 (m) | 1130 (m) | $\nu_{as}$ C—O—C |
| 1120 (m) | 1125 (w) | $\nu_s$ C—O—C |
| 1055 (s) | 1069 (s) | $\nu$ C—O |
| 1030 (s) | 1030 (s) | |
| | 1070 (s) | $\nu_{as}$ Si—O—Si |
| | 1030 (s) | |
| 980 (s) | 975 (s) | $\nu$ P—O—C |
| | 905 (m) | $\nu$ Si—C |
| 815 (w) | 800 (w) | $\rho$ $CH_3$ |

TABLE 2-continued

INFRARED ABSORPTIONS OF COMPOUND II AND POMS

| Absorption (cm$^{-1}$) | | Assignment |
|---|---|---|
| Compound II | POMS | |
| | 780 (m) | $\nu$ P—O |
| 750 (s) | | $\delta$ bonded O—H |

*attributed to absorbed water

The intrinsic viscosity of PMHS and POMS was measured in a chloroform solution at about 25°±0.1° C. using an Ubbelohole viscometer. The flow time employed was greater than 100 seconds. The intrinsic viscosities of the phosphorylated polysiloxanes are shown in Table III. As can be seen from this data, there was a steady increase in the viscosity as the molecular weight increased. It should also be noted that the intrinsic viscosity of POMS$_1$ was approximately 2.4 times greater then that of the prepolymer PHMS$_1$.

TABLE III

INTRINSIC VISCOSITY OF PMHS$_1$, PMHS$_2$, AND POMS$_1$ IN CHLOROFORM

| Polymer | Intrinsic Viscosity (cm$^3$g$^{-1}$) |
|---|---|
| PMHS$_1$ | 3.27 |
| PMHS$_2$ | 12.53 |
| POMS$_1$ | 7.88 |

POMS was found to be soluble in water having a low critical solution temperature at about 5.2° C. for POMS$_1$ and about 0° C. for POMS$_2$. The phase diagram was established for POMS$_1$, by plotting the temperature at which the polymer becomes completely soluble in water versus the concentration of the polymer at that temperature. This was used to establish the boundary. Table IV represents the temperature at which a given concentration of POMS$_1$ becomes insoluble in water. Below the temperature listed, for a given concentration, POMS$_1$ becomes soluble in water.

TABLE IV

CLOUD POINT TEMPERATURE OF POMS IN WATER

| Concentration (V %) | Temperature (°C.) |
|---|---|
| 1.00 | 6.2 |
| 1.64 | 5.2 |
| 4.76 | 5.6 |
| 6.25 | 6.0 |
| 9.10 | 6.8 |
| 11.10 | 7.4 |
| 14.30 | 8.8 |
| 20.00 | 11.1 |
| 33.30 | 16.8 |
| 40.00 | 19.9 |
| 50.00 | 26.9 |
| 57.14 | 33.5 |
| 62.50 | 44.7 |
| 66.70 | 60.7 |
| 70.00 | >100 |

A solution of 10% POMS$_1$ and 90% water was observed to be cloudy at room temperature, but was completely clear at about 7° C. A solution of 10% POMS$_1$, 30% isopropanol and 60% water, however, was observed to be clear even after four days at room temperature.

POMS$_1$ is also soluble in common polar organic solvents such as methanol, 95% ethanol, isopropanol, tetrahydrofuran and chloroform. However, POMS$_1$ is insoluble in aliphatic hydrocarbons such as hexane.

POMS$_2$ is only partially substituted and is soluble in both a polar (acetone) and a non-polar (hexane) solvent. The solubility of both POMS$_1$ and Compound 2 in different solvents is set forth in Table V. The solubility of POMS in these different solvents demonstrates that the POMS polymer is not crosslinked.

TABLE V

SOLUBILITY OF POMS AND COMPOUND II IN DIFFERENT SOLVENTS AT 21° C.

| Type | Solvent | POMS (and Compounds II) |
|---|---|---|
| Aromatic hydrocarbons | benzene | S* |
| | toluene | S |
| | xylene | S |
| Alcohols | methanol | S |
| | 95% ethanol | S |
| | cyclohexanol | S |
| | 2-methyl-butanol | S |
| | isopropanol | S |
| Ketones | acetone | S |
| | 2-butanone | S |
| Ethers | THF | S |
| | ethyl ether | S |
| | P-dioxane | S |
| N-containing solvents | N,N-dimethyl-acetamide | S |
| | pyridine | S |
| | triethylamine | I** |
| Chlorated solvents | chloroform | S |
| | carbon tetrachloride | S |
| Aliphatic hydrocarbons | hexane | I |
| | cyclohexane | I |
| | pentane | I |

*soluble
**insoluble

POMS$_1$ is a surface active polymer. The surface tension of an aqueous solution of POMS has been measured on the CAHN DCA 322 Dynamic Contact Angle Analyzer. Table VI illustrates the surface tensions of aqueous solutions of POMS at about 10° C. Critical micelle concentration ("CMC") of POMS is at the concentration of 0.003–0.006%. The temperature dependency of a aqueous solution of 0.1% POMS is shown in Table VII.

TABLE VI

SURFACE TENSION OF DIFFERENT CONCENTRATIONS OF POMS AQUEOUS SOLUTION AT 10° C.

| Concentration (10gL$^{-1}$) | Surface Tensions $\gamma$ (dynes cm$^{-1}$) |
|---|---|
| 5 × 10$^{-1}$ | 32.7 |
| 1 × 10$^{-1}$ | 33.9 |
| 5 × 10$^{-2}$ | 34.7 |
| 1 × 10$^{-2}$ | 36.6 |
| 5 × 10$^{-3}$ | 36.0 |
| 1 × 10$^{-3}$ | 49.0 |
| 5 × 10$^{-4}$ | 50.0 |
| 1 × 10$^{-4}$ | 55.0 |
| 5 × 10$^{-5}$ | 58.0 |
| 0 | 73.2 |

TABLE VII

SURFACE TENSIONS OF A 0.1% POMS AQUEOUS SOLUTION AT DIFFERENT TEMPERATURES

| Temperature (°C.) | Surface Tensions $\gamma$ (dynes cm$^{-1}$) |
|---|---|
| 0.1 | 33.8 |
| 1.9 | 34.0 |

TABLE VII-continued
SURFACE TENSIONS OF A 0.1% POMS AQUEOUS SOLUTION AT DIFFERENT TEMPERATURES

| Temperature (°C.) | Surface Tensions $\gamma$ (dynes cm$^{-1}$) |
| --- | --- |
| 3.9 | 33.9 |
| 5.9 | 33.5 |
| 10.6 | 33.9 |
| 14.2 | 34.8 |
| 17.1 | 34.7 |
| 23.0 | 35.2 |
| 35.0 | 35.3 |

EXAMPLE 2

The synthesis of a poly (methyl methoxysiloxane-methyl [2-(2', 2'-diethoxphosphonomethyl)-1,3-dioxane]5-oxysiloxane ("PMMOS") was achieved as follows.

The procedure previously described in Example 1 was followed to synthesize compound 2. About 3.2 grams of compound 2 and about 1 gram of PMHS, having a molecular weight of 2126, were dissolved in a 30% solution of tetrahydrofuran. The temperature was increased to about 60° C. About 80μ liters of zinc octanoate was then added to the solution and the reaction was allowed to proceed for approximately 48 hours. About 3 grams of methanol and 60μ liters of catalyst then were added and the solution was stirred for another 24 hours at about 60° C.

An IR analysis showed that the Si-H was fully substituted. The solvent and residual methanol were removed and the resulting copolymer was purified by precipitation from a 70:30 hexane-tetrahydrofuran mixture. The degree of substitution by compound 2 was found to be 65.2%.

The copolymer was found soluble in methanol, ethanol, tetrahydrofuran, p-dioxane and toluene but was insoluble in saturated hydrocarbons such as hexane. The cloud point of the PMMOS in a water solution at a concentration of 66.67% by volume was about −2.2° C. This compares with the cloud point of POMS with fully substituted phosphonate at the same concentration at about 60.7° C. The cloud point of phosphorylated polysiloxane decreased dramatically as the degree of substitution decreased.

EXAMPLE 3

Poly{[diethyl (phosphonobenzyl) α, β-ethyl]methylsiloxane}("PPEMS") was synthesized in two steps, as shown below. The first step was the hydrosilation of vinylbenzylchloride ("VBC") using platinum-divinyl-tetramethyldisiloxane complex as the catalyst. The second step was phosphorylation reaction employing the Arbuzov reaction.

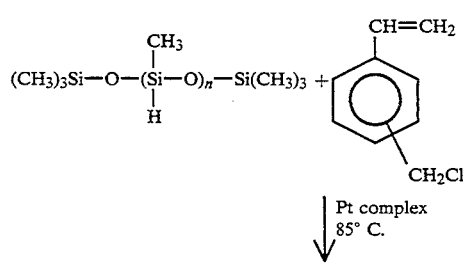

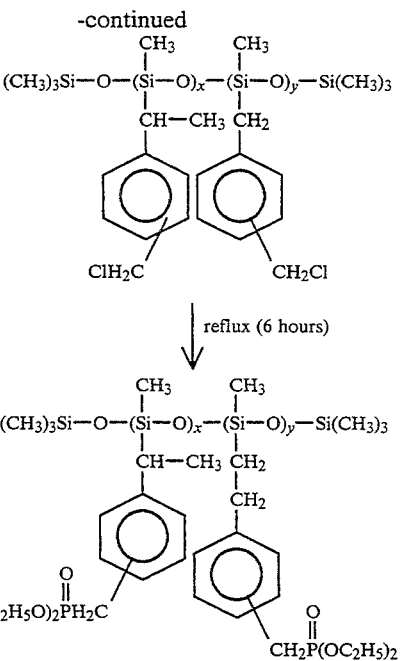

In the first step, approximately 32.0 grams of VBC was dissolved in about 29.50 grams of distilled toluene together with about 11.19 grams of PMHS. The average molecular weight of PMHS was determined to be 2126 by $^1$H NMR. To the above solution, 0.05 ml of catalyst was added. The reaction was carried out at approximately 85° C. for about 48 hours. The resulting product, poly [(chlorobenzyl) α,β-ethyl methyl siloxane] (compound 3), was purified by dissolving in toluene with carbon black to remove the catalyst and then with methanol to remove any unreacted VBC.

In the second step, 7.80 grams of compound 3 and 74.00 grams of predistilled triethylphosphite with excess triethylphosphite as the solvent were placed in a three-necked flask fitted with a magnetic stirrer, condenser and a nitrogen inlet. The reaction mixture was allowed to reflux for about 6 hours at approximately 156° C. under a gentle stream of nitrogen. The resulting pale yellow, viscous oil was purified under vacuum to remove any residual triethylphosphite.

The products of both steps were analyzed by $^1$H NMR on a 500 MHz spectrometer using CDCl$_3$ as a solvent. The analysis showed that the ratio of α:β was about 50:50 after the first step and remained the same after phosphorylation. The resulting product, PPEMS, was a sticky, transparent oil which was soluble in water-ethanol mixtures (e.g., 40% water by volume at 25° C.) and soluble in organic solvents, such as halogenated hydrocarbons, tetrahydrofuran, benzene, toluene, acetone, methanol, ethanol, p-dioxane and 2-ethoxyethylether and insoluble in saturated hydrocarbons such as cyclohexane.

The surface tension of an aqueous solution containing 0.02% of PPEMS, was measured as described in Example 1, and was found to be 38.7 dynes/cm at 22° C.

EXAMPLE 4

This example describes the ability of PPEMS to dissolve the complex metal salts of the transition metal, actinides, and lanthinides series. This property is most useful in solvent extraction of this metal-salt, in construction using paints and corrosion inhibitors and in medical implants where radiopacity of the implant material, due to the heavy metal-salt, is required.

The complexes were prepared by mixing the melted metal salt with liquid PPEMS at about 80° C. As such, the following metal-salt complexes containing various weight percents of PPEMS were prepared:

| Type of Metal Salt | In the PPEMS | |
|---|---|---|
| | Wt % | Wt % |
| (Transition Element) | | |
| $MnCl_2$ | 1.5 | 18 |
| $FeCl_3$ | 1.5 | 15 |
| $Cd(NO_3)_2$ | 1.5 | 20 |
| $Cu(NO_3)_2$ | 1.5 | 15 |
| (Group $V_A$) | | |
| $BiBr_3$ | 1.5 | 20 |
| $Bi(NO_3)_3$ | 1.5 | 20 |
| $Sb(NO_3)_3$ | 1.5 | 20 |
| (Lanthanide) | 1.5 | 7.0 |
| $PrCl_3$ | | |
| (Actinide) | 1.5 | 33 |
| $UO_2(NO_3)_2$ | | |

All complexes were clear (transparent) and showed the quality of a homogeneous miscible solid-solution. To further evaluate the nature of the resulting mixtures, mixtures with $UO_2(NO_3)_2$ were selected as representative of a high atomic weight metal salt.

The properties of the PPEMS-uranium complexes ("PU") were evaluated by differential scanning calorimetry ("DSC") on a Perkin Elmer DSC-4 calorimeter operating at a heating rate of 20° C./min. Each sample was scanned three times. The second scan was selected for determining the glass transition temperature ("Tg") of the polymer. The glass transition temperatures were taken at the midpoint of the heat capacity change during the transition. They are reported in Table VI. A significant increase in the glass transition temperature of the uranium-containing complexes was observed with an increase in the concentration of uranyl nitrate salt. The large increase in the glass transition temperature of the uranium-polymer complexes indicated a strong interaction between the two components.

TABLE VI

GLASS TRANSITION TEMPERATURE
OF PPEMS-URANYL NITRATE COMPLEXES

| Sample | Salt Content | | Tg |
|---|---|---|---|
| | (wt %) | (mole %) | (°C.) |
| PPEMS | 0 | 0 | −38.3 |
| $PU_1$ | 5.2 | 3.0 | −26.6 |
| $PU_2$ | 13.0 | 7.9 | −13.3 |
| $PU_3$ | 22.7 | 14.4 | 4.14 |
| $PU_4$ | 32.9 | 21.9 | 15.3 |

Radiographic analysis of the PPEMS-uranyl nitrate complexes was carried out with a Picker X-ray unit operating at 90 KV and 6 mA. Pellets of the complex (1 mm thick) along with an aluminum stepwedge with 1 mm steps were placed 22 inches below the tungsten anode on a Kodak ultraspeed double sided dental X-ray film No. DF49.

The results revealed that the radiopacity of the complexes increased as the concentration of the salt in the complex was increased. Furthermore, approximately 11% by weight of uranyl nitrate was found to achieve a radiopacity equivalent to 1 mm thick aluminum, the standard for medical applications.

EXAMPLE 5

Metal salts of transition group $V_a$, lanthanides and actinides were dissolved in $POMS_1$. When dissolved in low concentrations (i.e., less than 1 weight percent of organo-metal salts) viscous liquids were formed. When more than 3 weight percent were dissolved, a rubbery homogeneous material exhibiting different physical properties compared to the relevant properties of the metal salt were obtained. For example, paramagnetic paste of POMS-metal salt complex with the iron salt becomes progressively radiopaque with the heavier metal salt of bismuth and uranium.

The POMS salt complexes were prepared by dissolving the polymer in cold water and mixing it with a cold aqueous solution of the metal salt. The solution was then heated to above the LCST of the solution and the POMS-salt complex precipitated out. The precipitate was then dried in a vacuum oven at about 40° C. for 48 hours to yield a homogeneous salt complex. When high salt concentrations are used, the aqueous mixture yielded a solid polymer complex immediately upon mixing.

EXAMPLE 6

The synthesis of poly{4-methoxyl[(2-diethoxyphosphonomethyl)-1,3-dioxolane]methylsiloxane}("P-MOMS") was achieved as follows:

2-(1'-bromomethyl)-4-hydroxymethyl-1,3-dioxolane was synthesized essentially by the procedure as suggested by Piantadosi, et al (See C. Piantadosi, C. E. Anderson, E. A. Brecht, and C. L. Yarbro, *J. Am. Chem, Soc.*, 80, 6613 (1958)). 104.8 grams of bromoacetaldehyde diethyl/acetal was introduced into a flask equipped with a stirrer to which was added 48.97 grams of glycerol and 0.14 grams of a sulfosalicylic acid catalyst. The mixture was heated and stirred vigorously and the temperature gradually increased to about 130° C. The reaction was allowed to continue until the theoretical amount of ethanol was recovered. The mixture was then treated with a 5% potassium carbonate solution to neutralize the catalyst which was then extracted with ether. The ethereal extracts were washed with an additional 5% sodium carbonate solution and dried over magnesium sulfate. The ether was removed and a viscous oil was fractionated at about 82°-83° C. and 0.5 mm Hg. The yield was about 83%.

A phosphorylation reaction was then conducted to form [(2-diethylphosphonomethyl)]-4-hydroxymethyl-1,3-dioxolane (Compound 4). 68.65 grams of 2-(1'-bromomethyl)-4-hydroxymethyl-1,3-dioxolane which was synthesized as previously described was placed in a three-necked flask equipped with a magnetic stirrer and a nitrogen gas inlet. The mixture was heated gradually while stirring under a gentle stream of nitrogen. 57.25 grams of triethylphosphite was then added to the agitated solution dropwise over 30 minutes at a temperature of about 110° C. The temperature was then increased to about 156° C. and the reaction mixture was stirred at this temperature for about 10 hours. The mixture was fractionated at a temperature between 152° C. to 155° C. and 0.05 mm Hg and Compound 4 was collected at a yield of approximately 78%.

PMOMS was then synthesized via a condensation reaction between Compound 4 and PMHS having a molecular weight of 2126. The reaction conditions were the same as those described previously in Example 1.

The resulting PMOMS possessed similar solution properties as POMS. The PMOMS was found to be water soluble below 20° C. The surface tension of an aqueous solution of PMOMS at 10° C. was about 36 dynes/cm at 0.1 gL$^{-1}$.

EXAMPLE 7

2-propoxy-[-1,3-bis (diethoxyphosphonate)]methyl methoxymethyl siloxane copolymer ("PPOMS") was synthesized as follows:

1,3-bis(diethoxyphosphonate)-2-Propanol (Compound 5) was obtained by the phosphorylation of 1,3-dibromo-2-propanol via the Arbuzov reaction. About 19 grams of 1,3-dibromo-2-propanol was heated to about 120° C. while a gentle stream of nitrogen was bubbled through it. To this solution 33.92 grams of triethylphosphite was added dropwise over a period of approximately 40 minutes. The mixture was then heated to about 160° C. for approximately 5 hours. The excess triethylphosphite and monophosphonate was removed under vacuum to obtain Compound 5.

PPOMS was synthesized via a condensation reaction. About 6 grams of Compound 5 and about 1 gram of PMHS, having a molecular weight of 2126, were dissolved in a 30% solution of tetrahydrofuran. The temperature was increased to about 60° C. and about 85μ liters of zinc octanoate was added to the solution. The reaction was kept at a temperature of about 60° C. for approximately 72 hours. About 3 grams of methanol and 60μ liters of catalyst were then added and the solution was stirred for another 24 hours at a temperature of about 60° C. Infrared analysis showed disappearance of the Si-H bond of PMHS.

The resulting copolymer was purified by precipitation from a hexane-methanol mixture. The degree of substitution by Compound 5 was greater than 85%.

The resulting copolymer was soluble in acetone and was partially miscible in water at 25° C. Aqueous solutions of the resulting copolymer at concentrations of less than 0.1 gL$^{-1}$ were found to have a surface tensions of less than 40 dynes/cm.

EXAMPLE 8

This example describes the synthesis of phosphorylated polysiloxane copolymer ("POMOS") from 1,2:5,6-di-O-(2-diethoxyphosphonylethylidene) D-mannitol.

First, 1,2:5,6-di-O-bromoethylidene D-mannitol was synthesized employing the transacetalation reaction between about 43.10 grams of D-mannitol and about 91 grams bromoacetaldehyde diethyl acetal in the presence of about 0.15 grams of a sulfosalicyclic acid catalyst.

The Arbuzov reaction was then conducted between 23.61 grams of the resulting 1,2:5:6-di-O-bromoethylidene D-mannitol and about 18 grams of triethylphosphite to form 1,2:5,6-di-O-(2-diethoxyphosphonylethylidene) D-mannitol.

About 0.7 grams of PMHS having a molecular weight of 2126 and about 17.6 grams of the compound represented by Formula VI were dissolved in a 5% solution of tetrahydrofuran. The temperature was then increased to about 60° C. and about 60μ liters of zinc octanoate was added to the solution. The reaction time was about 72 hours. About 2 grams of methanol and 40μ liters of catalyst were then added and the solution was stirred for approximately 24 hours at a temperature about 60° C. The resulting copolymer was purified by repeated precipitation from a tetrahydrofuran-hexane mixture.

The resulting copolymer was soluble in alcohols, ethers, and partially miscible in water at 25° C. Aqueous solutions of the resulting copolymer at concentrations of less than 0.1 gL$^{-1}$ were found to have surface tensions of less than 39 dynes/cm.

Example 9

This example illustrates the synthesis of phosphorylated polysiloxane copolymer ("PMOOS") from 1,3:4,6-di-O-(2-diethoxyphosphonylethylidene) D-mannitol.

The procedures previously described in Example 1 was followed to obtain Compound 1. About 23 grams of Compound land about 8 grams of D-mannitol were allowed to react in the presence of approximately 20 ml. of concentrated hydrochloride acid as catalyst for about 8 days at a temperature of about 24° C. A colorless compound represented by Formula VII was recovered in a yield of about 80%.

The same procedures used to synthesize POMOS in Example 8 were followed to synthesize PMOOS. PMOOS exhibited similar solution properties as POMOS. Aqueous solutions of PMOOS at concentrations of less than 0.1 gL$^{-1}$ were found to have surface tensions of less than 39 dynes/cm.

EXAMPLE 10

This example shows the synthesis of phosphorylated polysiloxane ("POSOS") from 1,2:4,6-di-O-(2-diethoxyphosphonylethylidene)-D-sorbitol.

The first step was to synthesize di-0-bromoethylidene-D-sorbitol employing the procedures similar to the one used for preparing [2(1'-bromomethyl)-4-hydroxy-1,3-dioxolane]in Example 6. About 18 grams of sorbitol and about 39 grams of bromoacetaldehyde diethylacetal were allowed to react in the presence of approximately 0.1 grams of sulfosalicylic acid at about 140° C. to obtain the di-O-bromoethylidene-D-sorbitol. The yield was about 80%.

The second step was the phosphorylation reaction employing the Arbuzov reaction. About 14 grams of triethylphosphite and about 11.5 grams of 1,2:4,6-di-O-bromoethylidene-D-sorbitol were allowed to react by following the procedure used to synthesize the compound 4 described in Example 6. The percent yield was approximately 77%.

The same procedures used to synthesize POMOS in Example 8 were followed to synthesize POSOS. POSOS showed similar solution properties as POMOS. The polymer was soluble in acetone, alcohols, ethers, and partially in water at 20° C. Aqueous solutions of less than 0.1 gL$^{-1}$ were shown to have surface tensions of less than 38 dynes/cm.

EXAMPLE 11

Compound 1 was synthesized by following the procedures previously described in Example 1. To a mixture of about 9.5 grams of dipentaerythritol and about 17 grams of compound 1, approximately 15 ml of concentrated hydrochloric acid was added. The reaction mixture was stirred at a temperature of about 25° C. for approximately 10 days. The reaction mixture was neutralized with 2.5M aqueous sodium hydroxide. The compound represented by Formula IX was extracted with chloroform at a yield of approximately 85%.

About 0.6 grams of PMHS having a molecular weight of 2126 and 17.3 grams of the compound represented by Formula IX were dissolved in a 3% solution of tetrahydrofuran. The temperature was increased to approximately 65° C. and about 60μ liters of zinc octanoate was added to the solution. The reaction was allowed to proceed for approximately 72 hours. About 2 grams of methanol and 40μ liters of catalyst were then added and the solution was stirred for approximately 24 hours at about 60° C. The resulting copolymer was filtered out and the solvent was removed under vacuum. Finally, the copolymer was purified by the precipitation from a hexane - tetrahydrofuran mixture. The polymer was soluble in acetone, alcohols, ethers, and partially in water at 20° C. Aqueous solutions of less than 0.1 gL$^{-1}$ were shown to have surface tensions of less than 38 dynes/cm.

EXAMPLE 12

This example describes the synthesis of phosphorylated polysiloxane ("POOPS") from O,O-[1-(diethylphosphono)methyl]pentaerythriol.

Diethyl 2,2-diethoxyphosphonate (Compound 1) was synthesized as previously described in Example 1. To a suspension of about 34 grams pentaerythritol in water (75 ml), approximately 5 ml concentrated hydrochloric acid and approximately 64 grams of Compound 1 were added. The resulting mixture was stirred for about 24 hours at a temperature of about 25° C. The mixture was then neutralized with 2.5M NaOH solution, extracted with chloroform and dried overnight with anhydrous magnesium sulfate. The solvent was removed in a rotary evaporator and the concentrated product was washed with ethanol and dried under a vacuum. The compound represented by Formula X was obtained at a yield of approximately 62%.

About 0.9 grams of PMHS having a molecular weight of 2126 and about 13.6 grams of the compound represented by Formula X were then dissolved in a 5% solution of tetrahydrofuran. The temperature was increased to about 60° C. and about 70μ lites of zinc octanoate was added to the solution. The reaction was permitted to run for 48 hours and then about 2 grams of methanol and 40μ liters of catalyst were added. The solution was stirred for another 24 hours at a temperature of about 60° C. The resulting gel was filtered out from the solution and the solvent was removed in a rotary evaporator. The resulting copolymer was purified by precipitation from a hexane-methanol mixture.

The resulting POOPS was soluble in ethanol and tetrahydrofuran. Aqueous solutions of POOPS at concentrations of less than 0.1 gL$^{-1}$ were found to have surface tensions of less than 40 dynes/cm.

EXAMPLE 13

Example 2 was repeated except that ethylene glycol was used instead of methanol during the last stage of the reaction. The reaction mixture yielded 95% gel product which swelled in water, dimethyl formamide and other water-compatible solvents.

EXAMPLE 14

The reaction conditions previously described in Example 3 were followed with the exception that 26 grams of VBC were used. After the first step, the reaction mixture yielded 80% gel on which phosphorylation was conducted as described in the second step of Example 4. The resulting product of the reaction was a phosphorylated gel which swelled in water and other water-compatible solvents such as dimethyl formamide.

We claim:

1. A phosphorylated polysiloxane having the formula

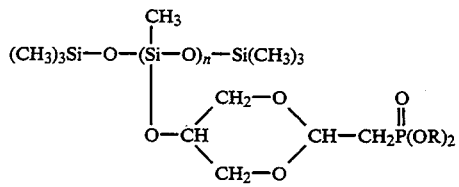

wherein R is independently a lower alkyl radical having up to eight carbon atoms and n, is an integer between 1 and 10,000.

2. A phosphorylated polysiloxane of claim 1 selected from the group consisting of poly{5-oxy[2-(2',2'-dimethoxyphosphonomethyl)- 1,3-dioxane]methylsiloxane}, poly{5-oxy[2-(2',2'-diethoxyphosphonomethyl)- 1,3-dioxane]methylsiloxane} and poly{5-oxy[2-(2',2'-dipropoxyphosphonomethyl)-1,3-dioxane]methylsiloxane}.

* * * * *

UNITED STATES PATENT AND TRADEMARK OFFICE
CERTIFICATE OF CORRECTION

PATENT NO. : 5,449,736
DATED : September 12, 1995
INVENTOR(S) : Cabasso, et al

It is certified that error appears in the above-indentified patent and that said Letters Patent is hereby corrected as shown below:

Column 1, line 57, please replace "Organo phosphates" with -- Organophophates --, Column 1, line 59, please replace "electrondonating" with -- electron donating --, Column 1, line 59, please replace "know" with -- known --, Column 2, line 18 before "provide" insert -- to --, Column 3, line 43, please replace "CHCH$_2$P(=O)(OC$_2$H$_5$" with -- CHCH$_2$P(=O)(OC$_2$H$_5$)$_2$ --, Column 4, line 43, please replace "completedly" with -- completely --, Column 6, line 58, please replace "hydrosilation" with -- hydrosilylation --, Column 7, line 9, please replace "hydrosilation" with -- hydrosilylation --,

UNITED STATES PATENT AND TRADEMARK OFFICE
CERTIFICATE OF CORRECTION

PATENT NO. : 5,449,736
DATED : September 12, 1995
INVENTOR(S) : Cabasso, et al.

It is certified that error appears in the above-indentified patent and that said Letters Patent is hereby corrected as shown below:

Column 7, line 18, please replace "hydrosilation" with -- hydrosilylation --,

Column 11, line 20, please replace "then" with -- than --,

Column 13, line 53, please replace "hydrosilation" with -- hydrosilylation --,

Column 14, line 41, please replace "three-necked" with -- three-neck --,

Column 16, line 54, please replace "three-necked" with -- three-neck --,

Column 18, line 15, please replace "was" with -- were --.

Signed and Sealed this

Fifth Day of March, 1996

Attest:

BRUCE LEHMAN

*Attesting Officer*  *Commissioner of Patents and Trademarks*